(12) United States Patent
Gjermansen et al.

(10) Patent No.: US 12,421,504 B2
(45) Date of Patent: Sep. 23, 2025

(54) BACTERIAL SUPEROXIDE DISMUTASES

(71) Applicant: Novozymes A/S, Bagsvaerd (DK)

(72) Inventors: Morten Gjermansen, Greve (DK); Dorotea Raventos Segura, Rungsted (DK)

(73) Assignee: Novozymes A/S, Bagsvaerd (DK)

( * ) Notice: Subject to any disclaimer, the term of this patent is extended or adjusted under 35 U.S.C. 154(b) by 214 days.

(21) Appl. No.: 18/029,582

(22) PCT Filed: Oct. 7, 2021

(86) PCT No.: PCT/EP2021/077790
§ 371 (c)(1),
(2) Date: Mar. 30, 2023

(87) PCT Pub. No.: WO2022/074164
PCT Pub. Date: Apr. 14, 2022

(65) Prior Publication Data
US 2023/0357729 A1 Nov. 9, 2023

(30) Foreign Application Priority Data
Oct. 7, 2020 (EP) .................................. 20200528.6

(51) Int. Cl.
*C12N 9/02* (2006.01)
*A23K 20/189* (2016.01)

(52) U.S. Cl.
CPC .......... *C12N 9/0089* (2013.01); *A23K 20/189* (2016.05); *C12Y 115/01001* (2013.01)

(58) Field of Classification Search
CPC .......... C12N 9/0089; C12Y 115/01001; A61K 38/446; A23K 20/189
See application file for complete search history.

(56) References Cited

U.S. PATENT DOCUMENTS

| | | |
|---|---|---|
| 4,106,991 A | 8/1978 | Markussen et al. |
| 10,104,902 B1 | 10/2018 | Zhu et al. |
| 2006/0073193 A1 | 4/2006 | Marcussen et al. |
| 2008/0003641 A1 | 1/2008 | Hsieh et al. |
| 2009/0092591 A1 | 4/2009 | Diehl |
| 2009/0220646 A1 | 9/2009 | Scott Street et al. |
| 2015/0140172 A1 | 5/2015 | Dale |
| 2015/0147451 A1 | 5/2015 | Reukov et al. |
| 2015/0342224 A1 | 12/2015 | Medoff |
| 2016/0165926 A1 | 6/2016 | Medoff |
| 2017/0333501 A1 | 11/2017 | Kim |
| 2018/0242615 A1 | 8/2018 | Marcussen et al. |
| 2019/0200653 A1 | 7/2019 | Ng et al. |

FOREIGN PATENT DOCUMENTS

| | | |
|---|---|---|
| CN | 101491290 A | 7/2009 |
| CN | 103667222 A | 3/2014 |
| CN | 104642749 A | 5/2015 |
| CN | 108522871 A | 9/2018 |
| CN | 108936001 A | 12/2018 |
| CN | 110373396 A | 10/2019 |
| EP | 2877043 A1 | 1/2014 |
| EP | 3447122 A1 | 2/2019 |
| EP | 3279319 B1 | 6/2020 |
| JP | 57036984 A | 2/1982 |
| KR | 950005178 A | 3/1995 |
| KR | 950028777 A | 11/1995 |
| KR | 101762199 B1 | 7/2017 |
| WO | 03009702 A1 | 2/2003 |
| WO | 2010004367 A1 | 1/2010 |
| WO | 2010115754 A1 | 10/2010 |
| WO | 2014014860 A1 | 1/2014 |
| WO | 2015035029 A1 | 3/2015 |
| WO | 2016134985 A1 | 9/2016 |
| WO | 2016186532 A1 | 11/2016 |
| WO | 2017040455 A1 | 3/2017 |
| WO | 2019138024 A1 | 7/2019 |
| WO | 2020053238 A1 | 3/2020 |
| WO | 2020144207 A1 | 7/2020 |
| WO | 2020200321 A1 | 10/2020 |
| WO | 2020200322 A1 | 10/2020 |

OTHER PUBLICATIONS

Bai et al., Poultry Science, 2017, 74-82, 96(1).
Danial et al., Journal of King Saud University, 2020, 2489-2494, 32(4).
Forest et al., J. Mol. Biol., 2000, 145-153, 296(1).
Jia et al., Scientific reports, 2018, 16712, 8(1).
Kang et al., Journal of crohn's and colitis, 2018, 860-869, 12(7).
Kuebutornye et al., Fish and Shellfish Immunology, 2019, 83-95, 97.
Liu et al, HAH Section F Structural Biology and Crystallization communications, 2007, 1003-1007, 63(12).
Sipos et al., EBI Accession No. A0A284S1G4, 2017.
Stephenie et al., Journal of Functional Foods, 2020, 1-10, 68.
Anonymous, Database UniProt accession No. A0A284S1G4.
Anonymous, 2025, DOD ID 29 alignment report—100% identity, 1-2.
Ferreira et al., 2003, Macromol. Biosci., 3, 179-188.
Kuo et al., 2015, GenBank Accession No. ETS03846.1.
Litta et al., 2018, DSM Vitamin E more than nature's most powerful antioxidant, 1-4.
Pariza et al., 2010, Regulatory Toxicology and Pharmacology, 56, 332-342.

*Primary Examiner* — Ruth A Davis
(74) *Attorney, Agent, or Firm* — Adam Rucker

(57) ABSTRACT

Polypeptides with superoxide dismutase activity of bacterial origin are useful in animal feed additives for improvement of animal growth and performance and in improving animal health, particularly animals exposed to environmental or heat stress.

14 Claims, No Drawings
Specification includes a Sequence Listing.

BACTERIAL SUPEROXIDE DISMUTASES

CROSS-REFERENCE TO RELATED APPLICATIONS

This application is a 35 U.S.C. 371 national stage entry of International Patent Application No. PCT/EP2021/077790, filed Oct. 7, 2021, and published as WO 2022/074164, which claims priority to European Patent Application No. 20200528.6, filed Oct. 7, 2020, the contents of each of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention also relates to new polypeptides of bacterial origin having superoxide dismutase activity and to animal feed additive or animal feed comprising superoxide dismutase of bacterial origin.

BACKGROUND OF THE INVENTION

Superoxide dismutase (SOD, EC 1.15.1.1) is an enzyme that alternately catalyzes the dismutation (or partitioning) of the superoxide ($O_2^-$) radical into either ordinary molecular oxygen ($O_2$) or hydrogen peroxide ($H_2O_2$). Superoxide is produced as a by-product of oxygen metabolism and, if not regulated, causes many types of cell damage. Thus, SOD is an important antioxidant defense in nearly all living cells exposed to oxygen. SODs are used in the pharmaceutical, cosmetic, food, and environmental protection industries due to their excellent antioxidant properties. Historically, SODs have been isolated from animal or plant sources, but the microbial sources organisms can be easily induced and cultivated on a large scale.

SODs naturally occur in many organisms such as plants, insects, birds, reptiles and mammals. Four types of SODs have been reported according to their metal cofactors: manganese SOD (Mn-SOD), iron SOD (Fe-SOD), copper/zinc SOD (Cu/Zn-SOD), and nickel SOD (Ni-SOD)$_2$.

Commercially available mammalian (bovine) SOD (Sigma), a Cu/Zn SOD, although having a high activity at neutral pH or at its optimal pH of 7.8, was found to lose 65% of its activity under gastric stability studies. According to its datasheet, its pH range is 7.6-10.5. Commercially available bacterial (from *E. coli*) Mn-SOD (S5639 from Sigma) was found to lose 57% of its activity under gastric stability studies.

Surprisingly, the inventors of the present invention found that SODs of bacterial origin that are highly active and provide beneficial effects when used in an animal feed or animal feed additive, alone or in combination with a catalase, to improve animal performance and/or health.

SUMMARY OF THE INVENTION

An aspect of the invention is directed to an isolated polypeptide having superoxide dismutase activity selected from the group consisting of:
a. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
b. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;
c. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;
d. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7;
e. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;
f. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;
g. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 13;
h. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
i. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;
j. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 19; and
k. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21.

A further aspect of the invention is directed to an isolated polypeptide of having superoxide dismutase activity selected from the group consisting of a. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;
b. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;
c. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;
d. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;
e. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;
f. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;
g. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;
h. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;
i. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and
j. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

A further aspect of the invention is directed to an isolated polynucleotide of bacterial origin encoding for a polypeptide having superoxide dismutase activity, wherein the polynucleotide is selected from the group consisting of
a. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;
b. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;
c. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;
d. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;
e. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;
f. polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;
g. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;
h. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;
i. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and
j. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

Relevant aspects of the invention are directed to a nucleic acid construct or expression vector comprising the polynucleotide as defined above and to a recombinant host cell transformed with the polynucleotide as defined above. In related aspects of the invention, a method of producing a polypeptide having superoxide dismutase activity, comprising: cultivating the host cell defined above under conditions suitable for expression of the polypeptide; and recovering the polypeptide is herein described.

An important aspect of the invention is directed to an animal feed additive comprising a polypeptide of bacterial origin having superoxide dismutase activity, preferably from a *Bacillus* species, a Neobacillus species, an Alkalihalobacillus species, a *Pedobacter* species, a *Novosphingobium* species, a Mongoliicoccus species, a *Variovorax* species, a Paraburkholderia species and a *Arcicella aquatica* species.

Alternatively, defined an animal feed additive comprises at least one and no more than two enzyme classes, wherein the at least one enzyme class is a superoxide dismutase of bacterial origin and the optional second enzyme class is a catalase.

An alternate aspect of the invention is directed to a method of improving one or more performance parameters in an animal comprising administering to the animal an animal feed or animal feed additive comprising one or more polypeptides having superoxide dismutase (SOD) activity of bacterial origin, wherein the one or more performance parameters is selected from the group consisting of the European Production Efficiency Factor (EPEF), Feed Conversion Ratio (FCR), Growth Rate (GR), Body Weight Gain (WG), Mortality Rate (MR) and Flock Uniformity (FU).

A method of improving or enhancing immune response and/or reducing inflammation and/or for the modulation of the gut flora in an animal comprising administering to the animal an animal feed or animal feed additive comprising one or more polypeptides having superoxide dismutase activity of bacterial origin is described herein.

A method of reducing or eliminating the use of antibiotics administered to an animal feed, comprising administering to the animal an animal feed or animal feed additive comprising of one or more polypeptides having superoxide dismutase activity of bacterial origin is described herein.

A further aspect of the invention is directed to use of an animal feed additive defined herein as an antioxidant, preferably in feed and feed premixes. Similarly, use of an animal feed additive defined herein for replacing or partially replacing antibiotics in animal feed is described herein.

An additional aspect is directed to an animal feed comprising one or more protein sources and one or more energy sources characterized in that the animal feed further comprises one or more polypeptides of bacterial origin having superoxide dismutase (SOD) activity, wherein the animal feed
  a. improves or enhances immune response; or
  b. reduces inflammation;
  when fed to the animal as compared to animals fed a feed composition without the polypeptides; and
  said feed optionally further comprising one or more polypeptides having catalase activity.

A granule, which comprises:
  a. a core comprising the polypeptide of the invention, and, optionally
  b. a coating consisting of one or more layer(s) surrounding the core is described herein.

An alternative aspect of the invention is a granule, which comprises:
  a. a core, and
  b. a coating consisting of one or more layer(s) surrounding the core, wherein the coating comprises the polypeptide of the invention.

A further aspect of the invention is directed to an animal feed comprising one or more protein sources and one or more energy sources characterized in that the animal feed further comprises one or more polypeptides of bacterial origin having superoxide dismutase (SOD) activity, wherein said polypeptide is as defined herein.

OVERVIEW OF SEQUENCE LISTING

SEQ ID NO:1 is the amino acid sequence of a mature polypeptide comprising 227 amino acid residues from Bacillus sp-62775 having superoxide dismutase (SOD) activity. Residues 1 to 21 represent the signal peptide.

SEQ ID NO:2 is the nucleotide sequence comprising 684 residues coding for the polypeptide having superoxide dismutase (SOD) activity of SEQ ID NO:1 from Bacillus sp-62775.

SEQ ID NO:3 is the amino acid sequence of a mature polypeptide comprising 179 amino acid residues from Bacillus sp-18780 having superoxide dismutase (SOD) activity. Residues 1 to 26 represent the signal peptide.

SEQ ID NO:4 is the nucleotide sequence comprising 540 residues coding for the polypeptide having superoxide dismutase (SOD) activity of SEQ ID NO:3 from Bacillus sp-18780.

SEQ ID NO:5 is the amino acid sequence of a mature polypeptide comprising 296 amino acid residues from Bacillus sp-17964 having superoxide dismutase (SOD) activity.

SEQ ID NO:6 is the nucleotide sequence comprising 891 residues coding for the polypeptide having superoxide dismutase (SOD) activity of SEQ ID NO:5 from Bacillus sp-17964.

SEQ ID NO:7 is the amino acid sequence of a mature polypeptide comprising 205 amino acid residues from Bacillus sp-62802 having superoxide dismutase (SOD) activity. Residues 1 to 22 represent the signal peptide.

SEQ ID NO:8 is the nucleotide sequence comprising 618 residues coding for the polypeptide having superoxide dismutase (SOD) activity of SEQ ID NO:7 from Bacillus sp-62802.

SEQ ID NO:9 is the amino acid sequence of a mature polypeptide comprising 261 amino acid residues from Variovorax boronicumulans having superoxide dismutase (SOD) activity. Residues 1 to 20 represent the signal peptide.

SEQ ID NO:10 is the nucleotide sequence comprising 786 residues coding for the polypeptide having superoxide dismutase (SOD) activity of SEQ ID NO:9 from Variovorax boronicumulans.

SEQ ID NO:11 is the amino acid sequence of a mature polypeptide comprising 174 amino acid residues from Bacillus sp-18318 having superoxide dismutase (SOD) activity.

SEQ ID NO:12 is the nucleotide sequence comprising 525 residues coding for the polypeptide having superoxide dismutase (SOD) activity of SEQ ID NO:11 from Bacillus sp-18318.

SEQ ID NO:13 is the amino acid sequence of a mature polypeptide comprising 245 amino acid residues from Pedobacter nyackensis having superoxide dismutase (SOD) activity. Residues 1 to 35 represent the signal peptide.

SEQ ID NO:14 is the nucleotide sequence comprising 738 residues coding for the polypeptide having superoxide dismutase (SOD) activity of SEQ ID NO:13 from Pedobacter nyackensis.

SEQ ID NO:15 is the amino acid sequence of a mature polypeptide comprising 255 amino acid residues from Mongoliicoccus sp-62519 having superoxide dismutase (SOD) activity. Residues 1 to 28 represent the signal peptide.

SEQ ID NO:16 is the nucleotide sequence comprising 768 residues coding for the polypeptide having superoxide dismutase (SOD) activity of SEQ ID NO:15 from Mongoliicoccus sp-62519.

SEQ ID NO:17 is the amino acid sequence of a mature polypeptide comprising 249 amino acid residues from Arcicella aquatica having superoxide dismutase (SOD) activity. Residues 1 to 26 represent the signal peptide.

SEQ ID NO:18 is the nucleotide sequence comprising 750 residues coding for the polypeptide having superoxide dismutase (SOD) activity of SEQ ID NO:17 from Arcicella aquatica.

SEQ ID NO:19 is the amino acid sequence of a mature polypeptide comprising 251 amino acid residues from Paraburkholderia *sediminicola* having superoxide dismutase (SOD) activity. Residues 1 to 30 represent the signal peptide.

SEQ ID NO:20 is the nucleotide sequence comprising 756 residues coding for the polypeptide having superoxide dismutase (SOD) activity of SEQ ID NO:19 from Paraburkholderia *sediminicola*.

SEQ ID NO:21 is the amino acid sequence of a mature polypeptide comprising 202 amino acid residues from *Bacillus licheniformis* having superoxide dismutase (SOD) activity.

DESCRIPTION OF THE INVENTION

The present invention relates to new polypeptides of bacterial origin having superoxide dismutase activity and to animal feed additive or animal feed comprising superoxide dismutase of bacterial origin.

The present invention also relates to the use of polypeptides of bacterial origin having superoxide dismutase activity in an animal feed or animal feed additive for improving any one of the performance parameter selected from the group consisting of
   improving one or more performance parameters, wherein the one or more performance parameters is selected from the group consisting of the European Production Efficiency Factor (EPEF), Feed Conversion Ratio (FCR), Growth Rate (GR), Body Weight Gain (WG), Mortality Rate (MR) and Flock Uniformity (FU),
   improving or enhancing immune response and/or reducing inflammation and/or for the modulation of the gut flora in an animal, and
   reducing or eliminating the use of antibiotics administered to animal feed.

Definitions

Animal: The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); pets such as cats and dogs; horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Bacterial origin: The term "bacterial origin" is intended to mean obtained, obtainable from or originating from a *Bacillus* species, a Neobacillus species, an Alkalihalobacillus species, a *Pedobacter* species, a *Novosphingobium* species, a Mongoliicoccus species, a *Variovorax* species, a Paraburkholderia species and a *Arcicella aquatica* species, most preferably a *Bacillus* species. Suitably, the said bacterial origin is selected from the group consisting of a *Bacillus subtilis, Bacillus licheniformis, Bacillus cereus, Bacillus circulans, Bacillus coagulans, Bacillus pseudomycoides, Bacillus lentus*, Neobacillus *bataviensis*, Alkalihalobacillus *hwajinpoensis, Arcicella aquatica*, Paraburkholderia *sediminicola, Pedobacter nyackensis, Variovorax boronicumulans*, Mongoliicoccus sp, *Novosphingobium* sp, and *Pedobacter soli*, preferably *Bacillus subtilis, Bacillus licheniformis, Bacillus cereus, Bacillus circulans, Bacillus coagulans, Bacillus pseudomycoides* and *Bacillus lentus*. In a preferred embodiment, the superoxide dismutase is not originating from *E. coli*.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Feed Conversion Ratio (FCR): FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. An FCR improvement of 2% means that the FCR was reduced by 2%.

Feed Premix: The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of microingredients in a larger mix. A premix according to the invention can be added to feed ingredients or to the drinking water as solids (for example as water soluble powder) or liquids.

European Production Efficiency Factor (EPEF): The European Production Efficiency Factor is a way of comparing the performance of animals. This single-figure facilitates comparison of performance within and among farms and can be used to assess environmental, climatic and animal management variables. The EPEF is calculated as [(liveability (%)×Liveweight (kg))/(Age at depletion (days)×FCR)]×100, wherein livability is the percentage of animals alive at slaughter, Liveweight is the average weight of the animals at slaughter, age of depletion is the age of the animals at slaughter and FCR is the feed conversion ratio at slaughter.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, *brassica* (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide or a catalytic domain having one or more (e.g., several) amino acids absent from the amino and/or carboxyl terminus of a mature polypeptide or domain; wherein the fragment has SOD activity.several) amino acids absent from the amino and/or carboxyl terminus of a mature polypeptide or domain; wherein the fragment has SOD activity.

Heat Stress: Heat stress occurs when an animal's heat load is greater than its capacity to lose heat. Pigs and other animals likely experience headaches, irritability and lethargy when they are too hot and have insufficient water. One or more of the following are typically observed with heat stress: increased breathing rate and sweating, increased water intake, decreased feed intake.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc.

Physical determination of the mature N terminus of SODs was done with Mass Spectrometry. Samples were diluted to 0.1 mg/ml in water. If they were to be deglycosylated before analysis, the samples were suspended in 50 mM Ammonium acetate buffer pH 5.5. The samples are then placed in an Ultimate 3000 UHPLC system (Thermo Scientific) at 8 degrees C. and run over an Advance Bio-RP desalting column (Agilent) The solvents used were A: LC/MS grade water with 0.1% formic acid, solvent: B 95% acetonitrile with 0.1% formic acid. The gradient was 5-80% B over 5 minutes. Post column the protein eluent was analyzed in a Bruker Maxis II mass spectrometer (Bremen Germany) and the resulting trace was analyzed by the supplied Bruker data analysis software. The deconvoluted spectrum was then compared to the calculated molecular weight with the expected N and C terminals using GPMAW (General Protein/Mass Analysis for Windows) software version 12.20. If the values match within 1 Dalton, a match was concluded.

Nutritional Stress: In pigs, poultry and other animals, symptoms of nutritional stress include impaired growth, immune suppression, reduced gut health, reduced gut integrity, shift in gut microflora and vomiting. In poultry, further symptoms include decreased egg production, decreased hatchability, gizzaed lesions, increased suspectibility to necrotic enteritis.

Obtained or obtainable from: The term "obtained or obtainable from" means that the polypeptide may be found in an organism from a specific taxonomic rank. If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. The skilled person can also compare the sequence to those of the application as filed. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Oxidative Stress: The term "oxidative stress" is intended to mean an imbalance between oxidants and reductants (antioxidants) at the cellular or individual level. Oxidative damage is one result of such an imbalance and includes oxidative modification of cellular macromolecules, cell death by apoptosis or necrosis, as well as structural tissue damage by means of reactive oxygen and nitrogen species (ROS, RNS).

Roughage: The term "roughage" means dry plant material with high levels of fiber, such as fiber, bran, husks from seeds and grains and crop residues (such as stover, copra, straw, chaff, sugar beet waste).

Secreted Enzyme: A secreted enzyme is an exoenzyme, or extracellular enzyme, in that is an enzyme that is secreted by a cell and functions outside that cell.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having SOD activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a SOD variant may comprise from 1 to 10 alterations, i.e. 1, 2, 3, 4, 5, 6, 7, 8, 9 or 10 alterations and have at least 20%, e.g., at least 40%, at least 50%, at least 60%, at least 70%, at least 80%, at least 90%, at least 95%, or at least 100% of the SOD activity of the parent SOD, such as SEQ ID NO: 1 to 5.

Nutrient: The term "nutrient" in the present invention means components or elements contained in dietary feed for an animal, including water-soluble ingredients, fat-soluble ingredients and others. The example of water-soluble ingredients includes but is not limited to carbohydrates such as saccharides including glucose, fructose, galactose and starch; minerals such as calcium, magnesium, zinc, phosphorus, potassium, sodium and sulfur; nitrogen source such as amino acids and proteins, vitamins such as vitamin B1, vitamin B2, vitamin B3, vitamin B6, folic acid, vitamin B12, biotin and phothenic acid. The example of the fat-soluble ingredients includes but is not limited to fats such as fat acids including saturated fatty acids (SFA); mono-unsaturated fatty acids (MUFA) and poly-unsaturated fatty acids (PUFA), fibre, vitamins such as vitamin A, vitamin E and vitamin K.

Polypeptides of Bacterial Origin Having Superoxide Dismutase Activity

Polypeptides of bacterial origin have been found to have superoxide dismutase activity. These polypeptides are suitable for use in animal feed.

One aspect of the invention is directed to an isolated polypeptide having superoxide dismutase activity selected from the group consisting of:
a. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
b. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;
c. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;
d. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7;
e. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;
f. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;
g. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 13;
h. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
i. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;
j. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 19; and
k. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21.

Alternatively defined, an aspect of the invention is directed to an isolated polypeptide of having superoxide dismutase activity selected from the group consisting of
a. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;
b. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;

c. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;

d. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;

e. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;

f. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;

g. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;

h. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;

i. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and j. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

The polypeptide having superoxide dismutase activity is of bacterial origin and typically originating from a bacteria selected from the group consisting of a *Bacillus* species, a Neobacillus species, an Alkalihalobacillus species, a *Pedobacter* species, a *Novosphingobium* species, a Mongoliicoccus species, a *Variovorax* species, a Paraburkholderia species and a *Arcicella aquatica* species, most preferably a *Bacillus* species. Suitably, the said bacterial origin is selected from the group consisting of a *Bacillus subtilis, Bacillus licheniformis, Bacillus cereus, Bacillus circulans, Bacillus coagulans, Bacillus pseudomycoides, Bacillus lentus*, Neobacillus bataviensis, Alkalihalobacillus hwajinpoensis, Arcicella aquatica, Paraburkholderia sediminicola, Pedobacter nyackensis, Variovorax boronicumulans, Mongoliicoccus sp, Novosphingobium sp, and Pedobacter soli, preferably *Bacillus subtilis, Bacillus licheniformis, Bacillus cereus, Bacillus circulans, Bacillus coagulans, Bacillus pseudomycoides* and *Bacillus lentus*.

The polypeptide having superoxide dismutase activity is an EC 1.15.1.1 super oxide dismutase (SOD) of bacterial origin. Preferably, it is not of *E. coli* origin.

The polypeptide of having superoxide dismutase activity is typically selected from the group consisting of a. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;

b. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;

c. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;

d. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;

e. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;

f. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;

g. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;

h. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;

i. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and j. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

Method of Producing a Polypeptide Having Superoxide Dismutase

The polypeptides of the invention are made by recombinant methods. Accordingly, an aspect of the invention, is a method of producing a polypeptide having superoxide dismutase activity, comprising: cultivating a host cell under conditions suitable for expression of the polypeptide; and recovering the polypeptide. The host cell is a recombinant host cell transformed with the polynucleotide as defined herein. Accordingly, a further aspect of the invention is a recombinant process comprising a nucleotide of bacterial origin, encoding for a polypeptide having superoxide dismutase activity, said nucleotide selected from the group consisting of a. polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;
b. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;
c. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;
d. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;
e. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;
f. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;
g. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;
h. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;
i. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and
j. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

A further aspect of the invention is directed to an isolated polynucleotide of bacterial origin encoding for a polypeptide having superoxide dismutase activity, wherein the polynucleotide is selected from the group consisting of a. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;
b. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;
c. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;
d. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;
e. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;
f. polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;
g. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;
h. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;
i. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and
j. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

A further aspect of the invention is directed to a nucleic acid construct or expression vector comprising the polynucleotide of the invention. A related aspect of the invention is directed to a transgenic plant, plant part or plant cell transformed with the polynucleotide of the invention. Similarly, as an aspect of the invention is directed to a method of producing the polypeptide of the invention comprising: i. cultivating a transgenic plant or a plant cell comprising a polynucleotide encoding the polypeptide under conditions conducive for production of the polypeptide; and ii. recovering the polypeptide.

The invention is furthermore directed to whole broth formulation or cell culture composition comprising the polypeptide having superoxide dismutase activity as defined herein.

Animal Feed and Animal Feed Additive

An important aspect of the invention is related to suitability of the polypeptides of the invention to be used in animal feed or as part of an animal feed additive. An animal feed additive comprising a polypeptide of bacterial origin having superoxide dismutase activity would benefit farmers and farm animals. The present invention also relates to the use of polypeptides of bacterial origin having superoxide dismutase activity in an animal feed or animal feed additive for improving any one of the performance parameter selected from the group consisting of
- improving one or more performance parameters, wherein the one or more performance parameters is selected from the group consisting of the European Production Efficiency Factor (EPEF), Feed Conversion Ratio (FCR), Growth Rate (GR), Body Weight Gain (WG), Mortality Rate (MR) and Flock Uniformity (FU),
- improving or enhancing immune response and/or reducing inflammation and/or for the modulation of the gut flora in an animal, and
- reducing or eliminating the use of antibiotics administered to animal feed.

In one aspect, the animal feed and animal feed additive further comprise a catalase. The animal feed additive may comprise an enzyme component, wherein the enzyme component comprises all of the enzymes of the additive and the enzyme component consists of a superoxide dismutase of bacterial origin and optionally of a catalase. Alternatively defined, the animal feed additive may comprise at least one and no more than two enzyme classes, wherein the at least one enzyme class is a superoxide dismutase of bacterial origin and the optional second enzyme class is a catalase.

The animal feed additive or animal feed comprises a polypeptide of bacterial origin, suitably a polypeptide as defined above.

The animal feed or feed additive may further comprise one or more polypeptides having catalase activity and/or further comprise one or more vitamins, suitably the one or more vitamins is a fat-soluble vitamin, preferably vitamin E.

A related aspect is directed to a use of an animal feed additive as defined above as an antioxidant, preferably in feed and feed premixes.

In view of the properties of superoxide dismutases, a related aspect is directed to a use of an animal feed additive as defined above for replacing or partially replacing antibiotics in animal feed.

One aspect is directed to an animal feed comprising one or more protein sources and one or more energy sources characterized in that the animal feed further comprises one or more polypeptides of bacterial origin having superoxide dismutase (SOD) activity, wherein the animal feed
a. improves or enhances immune response; or
b. reduces inflammation;
when fed to the animal as compared to animals fed a feed composition without the polypeptides; and
said feed optionally further comprising one or more polypeptides having catalase activity.

In relation to the feed additive, it may be formulated in various forms as know to the person skilled in the art. Accordingly, an aspect is directed to a granule, which comprises:
a. a core comprising a polypeptide of bacterial origin having superoxide dismutase activity, typically comprising the polypeptide defined above, and, optionally
b. a coating consisting of one or more layer(s) surrounding the core.

Alternative, the feed additive may be a granule, which comprises:
c. a core, and
d. a coating consisting of one or more layer(s) surrounding the core, wherein the coating comprises a polypeptide of bacterial origin having superoxide dismutase activity, typically comprising the polypeptide defined above.

A further aspect is directed to an animal feed comprising one or more protein sources and one or more energy sources characterized in that the animal feed further comprises one or more polypeptides of bacterial origin having superoxide dismutase (SOD) activity, wherein said polypeptide is as defined above.

A Method of Improving One or More Performance Parameters

The polypeptides of bacterial origin described herein when part of an animal feed or animal feed additive improve, according to an aspect of the invention, performance parameters in animals. Accordingly, the polypeptides allow for a method of improving one or more performance parameters in an animal comprising administering to the animal an animal feed or animal feed additive comprising one or more polypeptides having superoxide dismutase (SOD) activity of bacterial origin, wherein the one or more performance parameters is selected from the group consisting of the European Production Efficiency Factor (EPEF), Feed Conversion Ratio (FCR), Growth Rate (GR), Body Weight Gain (WG), Mortality Rate (MR) and Flock Uniformity (FU).

Accordingly, the polypeptides further allow for a method of improving or enhancing immune response and/or reducing inflammation and/or for the modulation of the gut flora in an animal comprising administering to the animal an animal feed or animal feed additive comprising one or more polypeptides having superoxide dismutase activity of bacterial origin.

The polypeptides further allow for a method of reducing or eliminating the use of antibiotics administered to an animal feed, comprising administering to the animal an animal feed or animal feed additive comprising of one or more polypeptides having superoxide dismutase activity of bacterial origin.

The polypeptide according to the method has superoxide dismutase activity, is of bacterial origin and typically originating from a bacteria selected from the group consisting of a *Bacillus* species, a Neobacillus species, an Alkalihalobacillus species, a *Pedobacter* species, a *Novosphingobium* species, a Mongoliicoccus species, a *Variovorax* species, a Paraburkholderia species and a *Arcicella aquatica* species, most preferably a *Bacillus* species. Suitably, the said bacterial origin is selected from the group consisting of a *Bacillus subtilis, Bacillus licheniformis, Bacillus cereus, Bacillus circulans, Bacillus coagulans, Bacillus pseudomycoides, Bacillus lentus*, Neobacillus bataviensis, Alkalihalobacillus *hwajinpoensis, Arcicella aquatica*, Paraburkholderia *sediminicola, Pedobacter nyackensis, Variovorax boronicumulans*, Mongoliicoccus sp, *Novosphingobium* sp, and *Pedobacter soli*, preferably *Bacillus subtilis, Bacillus licheniformis, Bacillus cereus, Bacillus circulans, Bacillus coagulans, Bacillus pseudomycoides* and *Bacillus lentus*.

The animal to which the animal feed or animal feed additive is fed according to the method, may have experienced heat stress, cold stress, nutritional stress and/or oxidative stress.

The method typically reduces cellular markers of reactive oxygen species or free radicals.

According to the method, the animal feed or animal feed additive may further comprise one or more polypeptides having catalase activity. The polypeptide having catalase activity is classified as an EC 1.11.1.6 catalase or as an EP 1.11.1.21 catalase peroxidase.

Preferred Embodiments

1. An isolated polypeptide having superoxide dismutase activity selected from the group consisting of:
   a. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
   b. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3;
   c. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5;
   d. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7;
   e. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;
   f. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;
   g. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 13;
   h. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
   i. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;
   j. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 19; and
   k. a polypeptide having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21.

2. An isolated polypeptide of having superoxide dismutase activity selected from the group consisting of
   a. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;
   b. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;
   c. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;
   d. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;
   e. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;
   f. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;
   g. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;
   h. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;
   i. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and j. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

3. A nucleotide of bacterial origin, encoding for a polypeptide having superoxide dismutase activity, said nucleotide selected from the group consisting of a. polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;

b. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;

c. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;

d. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;

e. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;

f. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;

g. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;

h. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;

i. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and j. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

4. The polypeptide as defined in any of embodiments 1 and 2, said polypeptide being of bacterial origin.

5. The polynucleotide according to embodiment 3, said polynucleotide being of bacterial origin.

6. The polypeptide according to embodiment 4, wherein the said bacterial origin is selected from the group consisting of a *Bacillus* species, a Neobacillus species, an Alkalihalobacillus species, a *Pedobacter* species, a *Novosphingobium* species, a Mongoliicoccus species, a *Variovorax* species, a Paraburkholderia species and a *Arcicella aquatica* species.

7. The polynucleotide according to embodiment 5, wherein the said bacterial origin is selected from the group consisting of a *Bacillus* species, a Neobacillus species, an Alkalihalobacillus species, a *Pedobacter* species, a *Novosphingobium* species, a Mongoliicoccus species, a *Variovorax* species, a Paraburkholderia species and a *Arcicella aquatica* species.

8. The polypeptide according to embodiment 6, wherein the said bacterial origin is selected from the group consisting of a *Bacillus subtilis, Bacillus licheniformis, Bacillus cereus, Bacillus circulans, Bacillus coagulans, Bacillus pseudomycoides, Bacillus lentus*, Neobacillus *bataviensis*, Alkalihalobacillus *hwajinpoensis, Arcicella aquatica*, Paraburkholderia *sediminicola, Pedobacter nyackensis, Variovorax boronicumulans*, Mongoliicoccus sp, *Novosphingobium* sp, and *Pedobacter soli*.

9. The polynucleotide according to embodiment 5, wherein the said bacterial origin is selected from the group consisting of a *Bacillus subtilis, Bacillus licheniformis, Bacillus cereus, Bacillus circulans, Bacillus coagulans, Bacillus pseudomycoides, Bacillus lentus*, Neobacillus *bataviensis*, Alkalihalobacillus *hwajinpoensis, Arcicella aquatica*, Paraburkholderia *sediminicola, Pedobacter nyackensis, Variovorax boronicumulans*, Mongoliicoccus sp, *Novosphingobium* sp, and *Pedobacter soli*.

10. An isolated polypeptide of having superoxide dismutase activity selected from the group consisting of a. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;

b. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;

c. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;

d. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;

e. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;

f. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;

g. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;

h. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;

i. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and j. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

11. An isolated polynucleotide of bacterial origin encoding for a polypeptide having superoxide dismutase activity, wherein the polynucleotide is selected from the group consisting of a. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 2;

b. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 4;

c. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 6;

d. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 8;

e. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 10;

f. polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 12;

g. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 14;

h. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 16;

i. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 18; and j. a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the polypeptide coding sequence of SEQ ID NO 20.

12. A nucleic acid construct or expression vector comprising the polynucleotide of embodiment 11.

13. A recombinant host cell transformed with the polynucleotide of embodiment 11.

14. A method of producing a polypeptide having superoxide dismutase activity, comprising:
cultivating the host cell of embodiment 13 under conditions suitable for expression of the polypeptide; and
recovering the polypeptide.

15. A transgenic plant, plant part or plant cell transformed with the polynucleotide of embodiment 11.

16. A method of producing the polypeptide of any one of embodiments 1-11 comprising:
i. cultivating a transgenic plant or a plant cell comprising a polynucleotide encoding the polypeptide under conditions conducive for production of the polypeptide; and
ii. recovering the polypeptide.

17. A whole broth formulation or cell culture composition comprising the polypeptide of any one of embodiments 1-11.

18. An animal feed additive comprising a polypeptide of bacterial origin having superoxide dismutase activity.

19. The animal feed additive according to embodiment 18 further comprising a catalase.

20. The animal feed additive according to embodiment 18 comprising an enzyme component, wherein the enzyme component comprises all of the enzymes of the additive and the enzyme component consists of a superoxide dismutase of bacterial origin and optionally of a catalase.

21. An animal feed additive comprising at least one and no more than two enzyme classes, wherein the at least one enzyme class is a superoxide dismutase of bacterial origin and the optional second enzyme class is a catalase.

22. The animal feed additive according to any of embodiments 18 to 21 wherein the polypeptide having superoxide dismutase activity is as defined in any of embodiments 1 to 11.

22. The animal feed additive according to any of embodiments 18 to 22 wherein the feed additive further comprises one or more polypeptides having catalase activity and/or further comprising one or more vitamins.

23. The animal feed additive of embodiment 22, wherein the one or more vitamins is a fat-soluble vitamin, preferably vitamin E.

21. A method of improving one or more performance parameters in an animal comprising administering to the animal an animal feed or animal feed additive comprising one or more polypeptides having superoxide dismutase (SOD) activity of bacterial origin, wherein the one or more performance parameters is selected from the group consisting of the European Production Efficiency Factor (EPEF), Feed Conversion Ratio (FCR), Growth Rate (GR), Body Weight Gain (WG), Mortality Rate (MR) and Flock Uniformity (FU).

22. A method of improving or enhancing immune response and/or reducing inflammation and/or for the modulation of the gut flora in an animal comprising administering to the animal an animal feed or animal feed additive comprising one or more polypeptides having superoxide dismutase activity of bacterial origin.

23. A method of reducing or eliminating the use of antibiotics administered to an animal feed, comprising administering to the animal an animal feed or animal feed additive comprising of one or more polypeptides having superoxide dismutase activity of bacterial origin.

24. The method according to any of embodiments 21 to 23, wherein the animal has experienced heat stress, cold stress, nutritional stress and/or oxidative stress.

25. The method of embodiments 21 to 24 to reduce cellular markers of reactive oxygen species or free radicals.

26. The method of any of embodiments 21 to 25, wherein the polypeptide having superoxide dismutase activity is an EC 1.15.1.1 super oxide dismutase (SOD) of bacterial origin.

27. The method of any of embodiments 21 to 26, wherein the polypeptide of bacterial origin having superoxide dismutase activity is as defined in any of embodiments 1 to 11.

28. The method of any of embodiments 21 to 27, wherein the polypeptide having superoxide dismutase (SOD) activity of bacterial origin is selected from the group consisting of a Cu-SOD, a Zn-SOD, a Mn-SOD, and an Fe-SOD.

29. The method according to any of embodiments 21 to 28, wherein the animal feed or animal feed additive further comprises one or more polypeptides having catalase activity.

30. The method according to any of embodiments 18 to 29, wherein the polypeptide having catalase activity is classified as an EC 1.11.1.6 catalase or as an EP 1.11.1.21 catalase peroxidase.

32. Use of an animal feed additive as defined in any of embodiments 11 to 17 as an antioxidant, preferably in feed and feed premixes.

33. Use of an animal feed additive as defined in any of embodiments 11 to 17 for replacing or partially replacing antibiotics in animal feed.

34. An animal feed comprising one or more protein sources and one or more energy sources characterized in that the animal feed further comprises one or more polypeptides pf bacterial origin having superoxide dismutase (SOD) activity, wherein the animal feed
  a. improves or enhances immune response; or
  b. reduces inflammation;
  when fed to the animal as compared to animals fed a feed composition without the polypeptides; and
  said feed optionally further comprising one or more polypeptides having catalase activity.

36. A granule, which comprises:
  a. a core comprising the polypeptide of any one of embodiments 1 to 11, and, optionally
  b. a coating consisting of one or more layer(s) surrounding the core.

37. A granule, which comprises:
  a. a core, and
  b. a coating consisting of one or more layer(s) surrounding the core, wherein the coating comprises the polypeptide of any one of embodiments 1 to 11.

38. A composition comprising the polypeptide of any one of embodiments 1 to 11 or the granule of embodiment 35 and 36.

39. An animal feed comprising one or more protein sources and one or more energy sources characterized in that the animal feed further comprises one or more polypeptides of bacterial origin having superoxide dismutase (SOD) activity, wherein said polypeptide is as defined in any one of embodiments 1 to 11.

EXAMPLES

Example 1: Cloning and Expression of Polypeptides

The DNA encoding the SOD genes of embodiments of the invention, from bacterial strains isolated from different countries are listed in table 1.

TABLE 1

| SEQ ID NO | Donor | Country of Origin |
| --- | --- | --- |
| SEQ ID NO: 1 | Bacillus sp-62775 | United States |
| SEQ ID NO: 3 | Bacillus sp-18780 | Denmark |
| SEQ ID NO: 5 | Bacillus sp-17964 | United States |
| SEQ ID NO: 7 | Bacillus sp-62802 | United States |
| SEQ ID NO: 9 | Variovorax boronicumulans | Germany |
| SEQ ID NO: 11 | Bacillus sp-18318 | Japan |
| SEQ ID NO: 13 | Pedobacter nyackensis | United States |
| SEQ ID NO: 15 | Mongoliicoccus sp-62519 | China |
| SEQ ID NO: 17 | Arcicella aquatica | United States |
| SEQ ID NO: 19 | Paraburkholderia sediminicola | Sweden |

The codon optimized synthetic DNA encoding the mature peptide sequences of the superoxide dismutases were ordered at the company TWIST Bioscience and cloned into the Bacillus expression vector described in WO 12/025577. Briefly, the DNA encoding the mature peptide of the SOD genes SEQ ID NO: 2, SEQ ID NO: 4 SEQ ID NO: 8 and SEQ ID NO: 10 were cloned in frame to a Bacillus clausii secretion signal, BcSP, with the following amino acid sequence: MKKPLGKIVASTALLISVAFSSSIASA (SEQ ID NO:23) whereas BcSP replaced the native secretion signal in the gene.

The DNA encoding the mature peptide of the SOD genes SEQ ID NO: 5 and SEQ ID NO:11 lacking a signal peptide in the natural protein, were cloned in the same vector without the BcSP Bacillus clausii secretion signal, to obtain intracellular expression.

Downstream of the SOD mature peptide sequences, an affinity tag sequence was introduced to ease the purification process (His-tag; with the following amino acid sequence: HHHHHH (SEQ ID NO: 24). The gene that was expressed therefore comprised the mature SOD sequence followed by the His tag sequence.

The final expression plasmids were transformed into a Bacillus subtilis expression host. The SOD genes were integrated by homologous recombination into the Bacillus subtilis host cell genome upon transformation.

The gene constructs were expressed under the control of a triple promoter system (as described in WO 99/43835). The gene coding for chloramphenicol acetyltransferase was used as maker (as described in (Diderichsen et al., 1993, Plasmid 30: 312-315)). Transformants were selected on LB media agar supplemented with 6 microgram of chloramphenicol per ml. One recombinant Bacillus subtilis clone containing each SOD expression construct was selected and was cultivated on a rotary shaking table in 500 ml baffled Erlenmeyer flasks each containing 100 ml yeast extract-based media. After 3-5 days cultivation time at 30° C. to 37° C., enzyme containing supernatants were harvested by centrifugation and the enzymes were purified by His-tag purification.

Example 2: His Tag Purification Method

The His-tagged SOD enzymes were purified by immobilized metal chromatography (IMAC) using Ni2+ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of t2e enzyme determined by Absorbance 280 nm after a buffer exchange in 50 mM HEPES, 100 mM NaCl pH7.0.

Example 3—Superoxide Dismutase Activity Determination

Principle:

Superoxide dismutases (SOD) catalyzes the reaction (dismutation) of superoxide anion into hydrogen peroxide and molecular oxygen. The activity is assayed as follow:

Superoxide-anions are formed enzymatically by xanthine oxidase from hypoxanthine. During the xanthine oxidase catalyzed reaction, hypoxanthine is transformed into hydrogen peroxide, uric acid and superoxide anions using atmospheric oxygen simultaneously. The water-soluble tetrazolium salt, WST-1, produces a water-soluble formazan dye upon reduction with a superoxide anion. The rate of WST-1 reduction to WST-1 formazan by superoxide anion is linearly related to the xanthine oxidase catalyzed superoxide anion formation and is inhibited by SOD. Absorbance at 450 nm is proportional to the amount of superoxide anion, the SOD activity as an inhibition activity can be quantified by measuring the decrease in the color development at 450 nm. Thus, the larger the activity of SOD, the slower the formation of the WST-1 formazan.

Method:

Mix 200 µl of a WST-1 working solution (1 mM WST-1 in 100 mM Tris-HCl, pH 8.0, 0.1 mM EDTA, 0.14 mM hypoxanthine, 0.0225% Brij) with 25 µl enzyme sample and 25 µl xanthine oxidase working solution (0,014 U/mL xanthine oxidase in 100 mM Tris-HCl, pH 8.0, 0.1 mM EDTA, 0.0225% Brij). Measure the change in absorption at 450 nm at a temperature of 30° C. for 30 minutes. In place of the enzyme sample, a buffer (blank) control is run, which will give maximum color development due to no inhibition from SOD activity.

Data Evaluation:

The slope of the Absorption as a function of time is determined for each enzyme and all tested enzyme concentrations. A standard curve was recorded using an enzyme standard with a known specific activity and the standard curve was corrected for non-linearity by the following function:

$$y = R_0 + K_c \times \frac{1}{1 + \exp(-(a + b * \ln(x)))}$$

Where y is the absorption of the standard for a known activity. The inverse of this formula is used to determine the activity for each enzyme and the slope of the so-obtained activity as a function of the enzyme concentration is calculated for each candidate, yielding the enzyme candidates specific activity. Then, the ratio of the slopes and the standard is calculated with the associated error as follows:

$$\text{Error} = \sqrt{\left(\frac{\text{Error of Enzyme candidate specific activity}}{\text{Enzyme candidate specific activity}}\right)^2 + \left(\frac{\text{Error of Standard specific activity}}{\text{Standard specific activity}}\right)^2}$$

Results

The table (Table 2) with the relative activity calculated relative to the commercially available SOD from Sigma (Commercially available bacterial (from *E. coli*) Mn-SOD (S5639 from Sigma))

TABLE 2

| SOD name | Relative activity | Donor Scientific Name |
| --- | --- | --- |
| Standard (Sigma SOD) | 100% | *E. coli* |
| SEQ ID NO: 1 | 1700% | *Bacillus* sp-62775 |
| SEQ ID NO: 3 | 1100% | *Bacillus* sp-18780 |
| SEQ ID NO: 5 | 800% | *Bacillus* sp-17964 |
| SEQ ID NO: 7 | 700% | *Bacillus* sp-62802 |
| SEQ ID NO: 9 | 600% | *Variovorax boronicumulans* |
| SEQ ID NO: 11 | 400% | *Bacillus* sp-18318 |
| SEQ ID NO: 13 | 400% | *Pedobacter nyackensis* |
| SEQ ID NO: 15 | 500% | *Mongoliicoccus* sp-62519 |
| SEQ ID NO: 17 | 400% | *Arcicella aquatica* |
| SEQ ID NO: 19 | 100% | *Paraburkholderia sediminicola* |
| SOD20-1 | 100% | *Bacillus lentus* |
| SOD32-1 | 0% | *Neobacillus bataviensis* |
| SOD34-1 | 200% | *Bacillus* sp-62615 |
| SOD19-1 | 0% | *Alkalihalobacillus hwajinpoensis* |
| SOD 7103 | 0% | *Rheinheimera* sp-64250 |
| SOD 7097 | 0% | *Rhizobium nepotum* |

The polypeptides of the invention were selected in that they outperform the commercially available bacterial SOD, from *E. coli*, available from Aldrich. As can be seen from the table *Bacillus* species performs well. A number of species did not perform well (not all data shown), as demonstrated by SODs at least from Alkalihalobacillus *hwajinpoensis*, *Rheinheimera* sp-64250, *Rhizobium* nepotum.

The invention claimed is:

1. A recombinant host cell transformed with a polynucleotide that encodes a polypeptide having superoxide dismutase activity, said polypeptide selected from the group consisting of:
   polypeptides having at least 80% identity to SEQ ID NO: 1;
   polypeptides having at least 80% identity to SEQ ID NO: 3;
   polypeptides having at least 80% identity to SEQ ID NO: 5;
   polypeptides having at least 80% identity to SEQ ID NO: 7;
   polypeptides having at least 80% identity to SEQ ID NO: 9;
   polypeptides having at least 80% identity to SEQ ID NO: 11;
   polypeptides having at least 80% identity to SEQ ID NO: 13;
   polypeptides having at least 80% identity to SEQ ID NO: 15; and
   polypeptides having at least 80% identity to SEQ ID NO: 17.

2. The recombinant host cell of claim 1, said polynucleotide selected from the group consisting of:
   polynucleotides having at least 80% identity to SEQ ID NO: 2;
   polynucleotides having at least 80% identity to SEQ ID NO: 4;
   polynucleotides having at least 80% identity to SEQ ID NO: 6;
   polynucleotides having at least 80% identity to SEQ ID NO: 8;
   polynucleotides having at least 80% identity to SEQ ID NO: 10;
   polynucleotides having at least 80% identity to SEQ ID NO: 12;
   polynucleotides having at least 80% identity to SEQ ID NO: 14;
   polynucleotides having at least 80% identity to SEQ ID NO: 16; and
   polynucleotides having at least 80% identity to SEQ ID NO: 18.

3. The recombinant host cell of claim 1, said polypeptide is a copper-containing superoxide dismutase.

4. The recombinant host cell of claim 1, said polypeptide is a zinc-containing superoxide dismutase.

5. The recombinant host cell of claim 1, said polypeptide is a manganese-containing superoxide dismutase.

6. The recombinant host cell of claim 1, said polypeptide is a iron-containing superoxide dismutase.

7. A method of producing a polypeptide having superoxide dismutase activity, said method comprising cultivating the recombinant host cell of claim 1 under conditions suitable for expression of said polypeptide having superoxide dismutase activity.

8. The method of claim 7, further comprising recovering said polypeptide having superoxide dismutase activity.

9. A method of producing an animal feed additive, said method comprising:
   incorporating a polypeptide produced according to the method of claim 7 into a carrier to form an animal feed additive.

10. The method of claim 9, wherein said polypeptide is incorporated into a granule comprising a core and one or more coating layers surrounding said core.

11. The method of claim 10, wherein said polypeptide is incorporated into the core of said granule.

12. The method of claim 10, wherein said polypeptide is incorporated into a coating layer of said granule.

13. An animal feed additive comprising a polypeptide having superoxide dismutase activity, said polypeptide selected from the group consisting of:
   polypeptides having at least 80% identity to SEQ ID NO: 1;
   polypeptides having at least 80% identity to SEQ ID NO: 3;
   polypeptides having at least 80% identity to SEQ ID NO: 5;
   polypeptides having at least 80% identity to SEQ ID NO: 7;
   polypeptides having at least 80% identity to SEQ ID NO: 9;
   polypeptides having at least 80% identity to SEQ ID NO: 11;
   polypeptides having at least 80% identity to SEQ ID NO: 13;
   polypeptides having at least 80% identity to SEQ ID NO: 15; and
   polypeptides having at least 80% identity to SEQ ID NO: 17.

14. The animal feed additive of claim 13, further comprising a catalase.

* * * * *

SEQUENCE LISTING

<160> NUMBER OF SEQ ID NOS: 21

<210> SEQ ID NO 1
<211> LENGTH: 227
<212> TYPE: PRT
<213> ORGANISM: Bacillus sp-62775
<220> FEATURE:
<221> NAME/KEY: PEPTIDE

<222> LOCATION: (22)..(227)

<400> SEQUENCE: 1

| Met | Lys | Arg | Phe | Leu | Phe | Leu | Thr | Leu | Leu | Leu | Cys | Met | Met | Phe | Val |
|---|---|---|---|---|---|---|---|---|---|---|---|---|---|---|---|
| 1 |  |  |  | 5 |  |  |  |  | 10 |  |  |  |  | 15 |  |

| Leu | Gly | Ala | Cys | Gly | Ser | Asp | Asn | Gly | Asn | Ser | Asn | Asn | Asn | Ala | Asn |
|---|---|---|---|---|---|---|---|---|---|---|---|---|---|---|---|
|  |  |  | 20 |  |  |  |  | 25 |  |  |  |  | 30 |  |  |

| Gly | Ile | Ser | Asp | Arg | Asp | Ser | Asn | Met | Glu | Lys | Ser | Asp | Glu | Arg | Ser |
|---|---|---|---|---|---|---|---|---|---|---|---|---|---|---|---|
|  |  | 35 |  |  |  |  | 40 |  |  |  |  | 45 |  |  |  |

| Ser | Val | Asp | Glu | Gly | Leu | Asn | Gln | Glu | Gly | Asn | Ser | Ala | Asn | Leu | Gly |
|---|---|---|---|---|---|---|---|---|---|---|---|---|---|---|---|
|  | 50 |  |  |  |  | 55 |  |  |  |  | 60 |  |  |  |  |

| Val | Glu | Gln | Asn | Asn | Pro | Gln | Gln | Lys | Asn | Gly | Gly | Val | Glu | Leu |
|---|---|---|---|---|---|---|---|---|---|---|---|---|---|---|
| 65 |  |  |  | 70 |  |  |  |  | 75 |  |  |  |  | 80 |

| Val | Thr | Val | Asp | Leu | Lys | Asp | Thr | Glu | Gly | Lys | Lys | Val | Gly | Thr | Val |
|---|---|---|---|---|---|---|---|---|---|---|---|---|---|---|---|
|  |  |  |  | 85 |  |  |  |  | 90 |  |  |  |  | 95 |  |

| Asn | Leu | Glu | Glu | Ile | Asp | Ala | Gly | Ile | Arg | Ile | Asp | Leu | Glu | Ala | Ser |
|---|---|---|---|---|---|---|---|---|---|---|---|---|---|---|---|
|  |  |  | 100 |  |  |  |  | 105 |  |  |  |  | 110 |  |  |

| Asn | Leu | Pro | Pro | Gly | Thr | His | Gly | Phe | His | Ile | His | Glu | Thr | Ala | Ser |
|---|---|---|---|---|---|---|---|---|---|---|---|---|---|---|---|
|  |  | 115 |  |  |  |  | 120 |  |  |  |  | 125 |  |  |  |

| Cys | Val | Ala | Pro | Thr | Phe | Glu | Ser | Ala | Gly | Gly | His | Phe | Asn | Pro | Thr |
|---|---|---|---|---|---|---|---|---|---|---|---|---|---|---|---|
| 130 |  |  |  |  | 135 |  |  |  |  | 140 |  |  |  |  |  |

| Asn | Ala | Ser | His | Gly | Val | Asp | Asn | Glu | Gly | Gly | Pro | His | Ala | Gly | Asp |
|---|---|---|---|---|---|---|---|---|---|---|---|---|---|---|---|
| 145 |  |  |  |  | 150 |  |  |  |  | 155 |  |  |  |  | 160 |

| Leu | Pro | Asn | Ile | Glu | Val | Gly | Lys | Asp | Gly | Thr | Ile | Lys | Glu | Glu | Ile |
|---|---|---|---|---|---|---|---|---|---|---|---|---|---|---|---|
|  |  |  | 165 |  |  |  |  | 170 |  |  |  |  | 175 |  |  |

| Thr | Ala | Lys | Asn | Val | Thr | Leu | Lys | Thr | His | Lys | Glu | Asn | Ser | Leu | Phe |
|---|---|---|---|---|---|---|---|---|---|---|---|---|---|---|---|
|  |  | 180 |  |  |  |  | 185 |  |  |  |  | 190 |  |  |  |

| Asp | Ser | Asp | Gly | Ser | Ala | Leu | Val | Ile | His | Ala | Lys | Ala | Asp | Asp | Asn |
|---|---|---|---|---|---|---|---|---|---|---|---|---|---|---|---|
|  | 195 |  |  |  |  | 200 |  |  |  |  | 205 |  |  |  |  |

| Lys | Ser | Gln | Pro | Ser | Gly | Asn | Ala | Gly | Asp | Arg | Ile | Ala | Cys | Ser | Glu |
|---|---|---|---|---|---|---|---|---|---|---|---|---|---|---|---|
| 210 |  |  |  |  | 215 |  |  |  |  | 220 |  |  |  |  |  |

| Ile | Gly | Glu |
|---|---|---|
| 225 |  |  |

<210> SEQ ID NO 2
<211> LENGTH: 684
<212> TYPE: DNA
<213> ORGANISM: Bacillus sp-62775
<220> FEATURE:
<221> NAME/KEY: gene
<222> LOCATION: (1)..(684)

<400> SEQUENCE: 2

```
atgaaacgat cctttttttt aacgcttctt ttgtgcatga tgtttgtact tgggcatgc      60
ggaagtgaca atggcaatag taataataac gcgaatggta ttagcgatag agatagcaac    120
atggaaaaaa gtgacgagag gtcttcggta gatgaagggt taaatcaaga agggaattca    180
gcaaatttgg gcgtggagca aaataatcct caacaaaaga atgaaggtgg ggtagagtta    240
gtgactgttg atttgaagga tacggaaggc aagaaagtgg gaacggtaaa cctcgaagaa    300
atcgatgccg ggattcgtat cgatttggag gcatcgaatt tgccaccggg aacacatggt    360
tttcatattc atgaaacagc atcatgcgtt gctccaactt ttgaatcagc aggcggtcat    420
tttaaccctac aaacgcgag ccacggtgtt gacaatgaag gaggaccaca tgcaggcgac    480
cttcccaata ttgaagtagg aaaagatggt acaattaaag aagaaataac agctaaaaat    540
gtcactttaa agacccacaa agaaaattca ttgttcgatt cagatggatc ggcgcttgtg    600
```

-continued

```
attcatgcca aagcggacga caataagtct cagccgtccg gtaatgcagg agatcgcatc    660
gcatgtagtg agattggtga atga                                          684
```

<210> SEQ ID NO 3
<211> LENGTH: 179
<212> TYPE: PRT
<213> ORGANISM: Bacillus sp-18780
<220> FEATURE:
<221> NAME/KEY: PEPTIDE
<222> LOCATION: (27)..(179)

<400> SEQUENCE: 3

```
Met Lys Lys Arg Tyr Phe Leu Ser Ala Leu Leu Thr Gly Met Val Leu
1               5                   10                  15

Phe Ser Gly Gln Thr Leu Asn Ala Gly His Ala Glu Lys Lys Gln Met
            20                  25                  30

Pro Val Lys Ile Thr Met Ile Asn Gln Asn Gly Lys Val Ser Gly Tyr
        35                  40                  45

Ala Thr Leu Thr Gln Thr Gln Met Gly Leu Asn Val Glu Val Asn Val
    50                  55                  60

Arg Gly Leu Lys Pro Gly Val His Gly Ile His Phe His Glu Asn Gly
65                  70                  75                  80

Ser Cys Ile Ala Pro Thr Phe Asp Ser Ala Gly Gly His Phe Asn Pro
                85                  90                  95

Glu His Lys Glu His Gly Leu Lys Asn Pro Met Gly Pro His Ala Gly
            100                 105                 110

Asp Leu Lys Asn Val Val Ala Asp Arg Asn Gly Val Leu Gln Thr Asn
        115                 120                 125

Phe Met Thr Ser Arg Val Thr Leu Gln Lys Gly Val Lys Asp Ser Leu
    130                 135                 140

Arg Asp Val Asn Ser Ser Ala Leu Val Ile His Ala Gln Glu Asp Asp
145                 150                 155                 160

Gln Lys Thr Asn Pro Ala Gly Asn Ser Gly Pro Arg Val Met Cys Gly
                165                 170                 175

Val Ile Lys
```

<210> SEQ ID NO 4
<211> LENGTH: 540
<212> TYPE: DNA
<213> ORGANISM: Bacillus sp-18780
<220> FEATURE:
<221> NAME/KEY: gene
<222> LOCATION: (1)..(540)

<400> SEQUENCE: 4

```
atgaaaaagc gctatttttt atccgctttg ttaacaggaa tggttttgtt ctccgggcaa     60
acgctaaatg caggccatgc tgaaaagaaa cagatgcctg tcaaaatcac tatgatcaat    120
caaaatggaa aagtctcagg gtatgcgaca ctcactcaaa cccagatggg cctgaacgtt    180
gaggtcaatg tacgtgggtt aaagcctggt gttcatggca ttcattttca tgaaaatggt    240
tcatgcattg ctccaacatt cgattcagct ggaggccact taatcccga acataaggag    300 cacggcctta aaaatccaat gggtccacat gccggcgatt taaaaaatgt ggtcgcggac    360
cgtaacgggg ttctgcaaac caactttatg acttcaagag tcaccccttca aaaaggtgtg    420 aaggacagtt tgcgtgatgt gaatagctcc gcattagtca ttcacgcaca agaagatgac    480
cagaaaacaa accccgctgg caattcaggc ccacgcgtca tgtgcggcgt gattaaatag    540
```

<210> SEQ ID NO 5
<211> LENGTH: 296
<212> TYPE: PRT
<213> ORGANISM: Bacillus sp-17964
<220> FEATURE:
<221> NAME/KEY: PEPTIDE
<222> LOCATION: (1)..(296)

<400> SEQUENCE: 5

Met Asp Ser Glu Arg Lys Thr Lys Gln Tyr Leu Met Glu Val Gln Asp
1               5                   10                  15

Trp Leu Gln Asn Val His Asp Phe Leu Asn Glu Gln Glu Ala Glu Ala
            20                  25                  30

Asp Pro Asp Phe Leu Ala Glu Ile Glu Arg Val Lys Asn Asp Val Lys
        35                  40                  45

Asn Gln Leu Ala Val Glu Thr Ile Ser Glu Ser Val Ile Ser Glu Leu
    50                  55                  60

Gln Gly Thr Val Gln Arg Met Asn Asn Arg Val Val Glu Leu Tyr Glu
65                  70                  75                  80

Arg Asn Gln Thr Arg Ile Arg Glu Ser Val Pro Ile Gly Lys His Val
                85                  90                  95

Leu Pro Pro Leu Pro Tyr Glu Tyr Asn Ala Leu Glu Pro Tyr Ile Ser
            100                 105                 110

Glu Glu Ile Met Arg Leu His His Thr Lys His His Gln Ser Tyr Val
        115                 120                 125

Asp Gly Leu Asn Lys Ala Glu Glu Lys Met Lys Gln Ala Arg Lys Arg
    130                 135                 140

Asn Asp Phe Asp Leu Ile Lys His Trp Glu Arg Glu Ala Ala Phe His
145                 150                 155                 160

Gly Ser Gly His Tyr Leu His Cys Ile Phe Trp Glu Ile Met Asn Pro
                165                 170                 175

Lys Gly Gly Gly Lys Pro Lys Gly Glu Leu Leu Ala Gln Ile Glu Lys
            180                 185                 190

His Phe Gly Ser Tyr Glu Leu Phe Lys Lys His Phe Ser Glu Ala Ala
        195                 200                 205

Lys Lys Val Glu Gly Val Gly Trp Ala Ile Leu Val Trp Ser Pro Arg
    210                 215                 220

Ser Arg Lys Leu Glu Ile Leu Gln Ala Glu Arg His Gln Phe Leu Thr
225                 230                 235                 240

Gln Trp Asp Thr Ile Pro Ile Leu Val Leu Asp Val Trp Glu His Ala
                245                 250                 255

Tyr Tyr Leu Gln Tyr Lys Asn Asp Lys Gly Thr Tyr Val Asp Gln Trp
            260                 265                 270

Trp Asn Val Val Tyr Trp Pro Asn Ala Glu Lys Arg Phe Ala Glu Ala
        275                 280                 285

Lys Lys Leu Lys Trp Glu Pro Tyr
    290                 295

<210> SEQ ID NO 6
<211> LENGTH: 891
<212> TYPE: DNA
<213> ORGANISM: Bacillus sp-17964
<220> FEATURE:
<221> NAME/KEY: gene
<222> LOCATION: (1)..(891)

<400> SEQUENCE: 6

```
atggattctg aaagaaaaac gaaacaatat ttaatggaag tgcaagactg gctgcaaaac      60
gttcatgatt ttctgaatga gcaagaggcg gaagcggatc cagatttttt ggccgagatt     120
gagcgtgtaa aaaatgatgt gaagaatcaa cttgcggtag aaaccataag tgagtcggtt     180
atatccgaac ttcaaggtac cgttcagcga atgaacaatc gtgtcgtcga attatatgaa     240
agaaatcaaa caagaattcg tgaatccgtg ccgatagggaa acatgtact tccgccatta     300
ccatatgaat acaacgcctt agaaccttat attagcgaag aaatcatgag gctccaccat     360
acaaaacatc atcaaagtta tgtagatggg ctaaataaag ccgaagaaaa aatgaagcaa     420
gcaagaaaaa ggaatgattt tgatttaatt aaacattggg aacgagaagc cgcctttcac     480
gggtcgggac attatctgca ttgtatctttt tgggaaatta tgaatcctaa aggcggtgga     540
aaaccaaaag gagagcttct tgctcaaatc gaaaaacatt ttggcagcta tgagttattt     600
aaaaagcatt tttcagaagc agctaaaaaa gttgaagggg taggatgggc tattttagtt     660
tggtcgcccc gatcgcgaaa actggaaatt ttgcaagcag agcgccatca atttttaaca     720
cagtgggata ccatcccgat tcttgttctg atgtttggg agcatgccta ttacttgcaa     780
tataaaaatg ataaaggaac gtatgtagat caatggtgga acgtagttta ttggccaaat     840
gcagaaaaaa gatttgccga agcaaaaaaa ctcaaatggg aaccttatta a               891
```

<210> SEQ ID NO 7
<211> LENGTH: 205
<212> TYPE: PRT
<213> ORGANISM: Bacillus sp-62802
<220> FEATURE:
<221> NAME/KEY: PEPTIDE
<222> LOCATION: (23)..(205)

<400> SEQUENCE: 7

Met Ser Lys Met Tyr His Tyr Leu Leu Leu Ile Val Ile Gly Leu Leu
1               5                   10                  15

Leu Thr Ser Ala Cys Ala Glu Lys Gln Val Met Glu Phe Gly Glu Gln
            20                  25                  30

Pro Leu Met Leu Asp Asp Val Glu Ala Lys Ala Asp Ile Tyr Asp Lys
        35                  40                  45

Glu Gly Glu Met Met Gly Asp Val Val Phe Ser Phe Ile Asp Asp Lys
    50                  55                  60

Val Leu Ile Gln Ala Asp Val Gln Asn Leu Pro Pro Gly Trp His Gly
65                  70                  75                  80

Phe His Ile His Glu Asn Gly Ser Cys Gly Leu Thr Glu Gln Gly Ala
                85                  90                  95

Asp Phe Ser Lys Ala Gly Gly His Phe His His Ala Asp Asp Gly Gln
            100                 105                 110

His Gly Tyr His Ala Gly Asp Met Pro Pro Leu Tyr Val Asn Glu Asn
        115                 120                 125

Gly His Ala Tyr Met Thr Val Leu Met Asp Arg Phe Ser Leu Asp Glu
    130                 135                 140

Val Leu Ser Gly Asn Gly Thr Ser Val Ile Ile His Glu Glu Pro Asp
145                 150                 155                 160

Asn Leu Gly His Ile Pro Glu Arg Tyr Gln Ser Val Lys Ser Asp Gln
                165                 170                 175

Pro Gly Pro Asp Glu Gln Thr Leu Ala Thr Gly Asp Gly Gly Ser Arg
            180                 185                 190

Leu Ala Cys Gly Glu Ile Lys Arg Val Glu Lys Glu Glu

<210> SEQ ID NO 8
<211> LENGTH: 618
<212> TYPE: DNA
<213> ORGANISM: Bacillus sp-62802
<220> FEATURE:
<221> NAME/KEY: gene
<222> LOCATION: (1)..(618)

<400> SEQUENCE: 8

```
atgagtaaaa tgtatcatta ccttcttctg attgtcatcg gcttattatt gacaagtgca      60
tgcgcagaga agcaagtaat ggagtttggt gaacaaccgc ttatgcttga cgatgtggaa     120
gcgaaagcgg acatatacga taaagaagga gaaatgatgg gagatgtcgt ttttcattt      180
attgatgata aggttctcat ccaagccgat gttcaaaatt tgcccccagg atggcatggg     240
ttccatattc atgaaaatgg ttcttgtggc ttgactgaac aaggagccga ttttccaaa      300
gcaggaggtc actttcatca tgcagacgat ggacagcatg gctatcatgc aggagatatg     360
ccaccgctgt acgtcaacga aaatggtcat gcttatatga cggttcttat ggaccgcttt     420
tcattagatg aagtgctaag tggcaatgga acgtcagtca tcattcacga ggaaccagat     480
aatcttggtc atatcccaga acgttatcaa tctgttaaaa gcgatcagcc aggaccagat     540
gaacaaacac tagctacggg agatgggggt agtcgtttag cttgtggaga aattaaacgc     600
gtagagaaag aagaataa                                                    618
```

<210> SEQ ID NO 9
<211> LENGTH: 261
<212> TYPE: PRT
<213> ORGANISM: Variovorax boronicumulans
<220> FEATURE:
<221> NAME/KEY: PEPTIDE
<222> LOCATION: (21)..(261)

<400> SEQUENCE: 9

```
Met Gln Arg Phe Ile Val Ser Leu Ala Val Ala Gly Phe Val Ala Gly
1               5                   10                  15

Cys Ala Gln Thr Gly Pro Met Ser Ala Gln Ser Met Thr Pro Ala Ala
            20                  25                  30

Pro Met Ala Pro Ala Pro Met Ala Ala Pro Met Ala Pro Pro Pro
        35                  40                  45

Pro Ala Thr Pro Pro Ala Ala Gln Val Phe Arg Gln Ala Pro Leu Pro
    50                  55                  60

Tyr Ala Ala Asp Ala Leu Glu Pro Val Ile Asp Lys Ala Thr Met Glu
65                  70                  75                  80

Ile His His Gly Arg His His Lys Ala Tyr Tyr Asp Ala Leu Asn Asn
                85                  90                  95

Ala Ala Ala Ser Ser Pro Glu Val Ala Arg Ser Thr Leu Glu Gln Leu
            100                 105                 110

Val Ala Thr Ala Ser Arg Gln Thr Met Val Val Arg Asn Asn Ala Gly
        115                 120                 125

Gly Ala Trp Asn His Ala Phe Phe Trp Asn Thr Met Ala Pro Ala Gly
    130                 135                 140

Gln Arg Gly Ala Pro Ser Pro Ala Leu Met Ala Arg Val Gln Ala Asp
145                 150                 155                 160

Phe Gly Ser Met Glu Thr Leu Met Arg Gln Phe Asn Gln Ala Gly Ala
                165                 170                 175
```

Ser Arg Phe Gly Ser Gly Trp Ala Trp Leu Ile Val Lys Asp Gly Lys
            180                 185                 190

Leu Ala Val Ser Ser Thr Pro Asn Gln Asp Asn Pro Leu Met Asp Val
        195                 200                 205

Ala Glu Val Arg Gly Thr Pro Ile Leu Gly Asn Asp Val Trp Glu His
    210                 215                 220

Ala Tyr Tyr Leu Lys Tyr Gln Asn Arg Arg Ala Asp Tyr Leu Ala Ala
225                 230                 235                 240

Trp Trp Gln Val Val Asn Trp Asn Glu Val Asn Arg Arg Phe Ala Ala
                245                 250                 255

Ala Thr Ala Ala Arg
        260

<210> SEQ ID NO 10
<211> LENGTH: 786
<212> TYPE: DNA
<213> ORGANISM: Variovorax boronicumulans
<220> FEATURE:
<221> NAME/KEY: gene
<222> LOCATION: (1)..(786)

<400> SEQUENCE: 10
atgcagagat tcatcgtgtc gctcgcggtc gcgggtttcg tcgccggatg cgcgcagacc      60
ggccccatgt cggcccagtc catgacgccc gccgctccca tggcgcccgc ccgatggcc     120 gcgcccatgg caccgccgcc accgcccgcg accccgcccg ccgcccaggt gttccgccag     180
gcgccgttgc cctatgcggc cgacgcgctg gagccggtga tcgacaaggc gacgatggag     240
atccatcacg gccgccatca caaggcctac tacgacgcgt tgaacaacgc cgccgcctcg     300
agccccgagg tcgcgcgctc gaccctcgaa cagctcgtcg ccaccgcatc cgcgcagacg     360
atggtcgtgc gcaacaacgc cggcggcgcc tggaaccatg ccttcttctg gaacaccatg     420
gcaccggccg ccagcgcggc gcgccgtcg cccgcgctga tggcgcgcgt ccaggccgac     480
ttcggctcca tggagacgct gatgcgccag ttcaaccagg ccggcgcctc gcgcttcggt     540
tccggctggg cctggctgat cgtcaaggac ggcaagctcg ccgtcagctc cacgcccaac     600
caggacaacc cattgatgga cgtggccgaa gtgcgtggca cgcccatcct gggcaacgac     660
gtctgggagc atgcctacta cctgaagtac cagaaccgtc gcgccgacta tctcgccgcc     720
tggtggcagg tggtgaactg gaacgaagtc aaccgccgct cgccgccgc gaccgccgcg     780 cgctga                                                              786

<210> SEQ ID NO 11
<211> LENGTH: 174
<212> TYPE: PRT
<213> ORGANISM: Bacillus sp-18318
<220> FEATURE:
<221> NAME/KEY: PEPTIDE
<222> LOCATION: (1)..(174)

<400> SEQUENCE: 11

Met Asn Tyr Tyr Gln Tyr Gly Tyr Pro Ala Tyr Ser Tyr Tyr Pro Tyr
1               5                   10                  15

Arg Asn Met Pro Ala Met Ala Tyr Ala Ile Ile Gln Gly Gly Pro Leu
            20                  25                  30

Ala Pro Lys Leu Asn Gly Tyr Ile Phe Phe Arg Glu Val Pro Asn Gly
        35                  40                  45

Val Glu Ala Phe Ile Glu Ile Asn Gly Leu Pro Gln Tyr Gln Lys Gly
    50                  55                  60

```
Ser Gly Asp Asn Lys Pro Val Gly Pro His Gly Phe His Leu His Glu
 65                  70                  75                  80

Lys Gly Val Cys Glu Val Gly Asp Glu Glu Asp Pro Phe Gln Ser Ala
                 85                  90                  95

Gly Gly His Trp Asn Pro Asp Asn Gln Pro His Gly Asn His Ala Gly
            100                 105                 110

Asp Phe Pro Val Leu Phe Ser Asn Asp Gly Tyr Ser Lys Met Ser Phe
        115                 120                 125

Phe Thr Asn Arg Phe Lys Val Asp Asp Val Ile Gly Lys Gly Val Ile
130                 135                 140

Ile His Gln Asn Pro Asp Asp Tyr Arg Ser Gln Pro Ser Gly Asp Ala
145                 150                 155                 160

Gly Lys Arg Leu Gly Cys Gly Val Ile Thr Lys Tyr Gly Met
                165                 170
```

<210> SEQ ID NO 12
<211> LENGTH: 525
<212> TYPE: DNA
<213> ORGANISM: Bacillus sp-18318
<220> FEATURE:
<221> NAME/KEY: gene
<222> LOCATION: (1)..(525)

<400> SEQUENCE: 12

```
atgaattatt atcaatacgg ctatcctgcc tattcatatt atccttatag aaatatgcct      60
gcgatggcat atgccatcat tcagggaggc ccactcgctc ccaagttaaa cggatatatc     120
ttctttcggg aagttccgaa tggagtagaa gcattcatag agataaatgg actgccgcag     180
tatcaaaaag gaagcggtga taataagcca gttgggccgc atggctttca tcttcatgaa     240
aaaggagtat gtgaagtcgg agacgaggag gatcctttc aatctgcagg aggacattgg     300
aatccggata tcagccgca tggaaatcac gcaggagatt ttccggtact gttctcaaac     360
gatggctaca gtaaaatgtc ttttttttacg aacaggttca agtggatga tgtcatcgga     420 aaaggagtga tcatccacca aaatccggat gactatagat cccagccttc cggggatgca     480
gggaagaggc tcggctgtgg agtgattacg aagtatggaa tgtag                     525
```

<210> SEQ ID NO 13
<211> LENGTH: 245
<212> TYPE: PRT
<213> ORGANISM: Pedobacter nyackensis
<220> FEATURE:
<221> NAME/KEY: PEPTIDE
<222> LOCATION: (36)..(245)

<400> SEQUENCE: 13

```
Met Glu Thr Asn Thr Arg Arg Asp Phe Ile Lys Thr Thr Leu Thr Ala
  1               5                  10                  15

Ser Leu Ala Val Val Ile Gly Thr Pro Val Leu Leu Ser Gly Gly Thr
                 20                  25                  30

Ala Leu Ala Ala Ala Val Thr Ala Glu Glu Gly Thr Gly Phe Ala Ala
             35                  40                  45

Leu Lys Phe Ala Gln Val Pro Leu Lys Tyr Ala Phe Asn Ala Leu Glu
         50                  55                  60

Pro Asn Ile Asp Ala Leu Thr Met Asp Ile His Tyr Thr Lys His His
 65                  70                  75                  80

Ala Ala Tyr Val Lys Asn Val Asn Asp Ala Ile Ala Ala Glu Lys Ile
                 85                  90                  95
```

```
Pro Tyr Lys Thr Glu Ala Glu Phe Phe Asn Asn Ala Ser Lys Leu Ser
            100                 105                 110

Ala Lys Ala Arg Asn Asn Gly Gly Ala Trp Asn His Asn Phe Phe
        115                 120                 125

Phe Glu Thr Leu Lys Pro Gly Gly Ala Thr Gly Pro Glu Gly Lys Leu
    130                 135                 140

Lys Asp Ala Ile Val Lys Ser Phe Val Ser Val Asp Lys Phe Lys Glu
145                 150                 155                 160

Gln Phe Ser Ala Ala Ala Ser Arg Phe Gly Ser Gly Trp Ala Trp
            165                 170                 175

Leu Val Asn Asp Lys Gly Thr Leu Lys Ile Cys Ser Thr Ala Asn Gln
        180                 185                 190

Asp Asn Pro Leu Phe Asp Asn Ala Glu Val Lys Gly Val Pro Leu Leu
    195                 200                 205

Gly Leu Asp Val Trp Glu His Ala Tyr Tyr Leu Lys Tyr Gln Asn Lys
    210                 215                 220

Arg Ala Asp Tyr Ile Ala Asn Trp Trp Asn Val Val Asp Trp Asp Val
225                 230                 235                 240

Val Ser Lys Arg Leu
            245

<210> SEQ ID NO 14
<211> LENGTH: 738
<212> TYPE: DNA
<213> ORGANISM: Pedobacter nyackensis
<220> FEATURE:
<221> NAME/KEY: gene
<222> LOCATION: (1)..(738)

<400> SEQUENCE: 14
atggaaacaa acacccgaag agactttatt aaaactacgt tgacggcctc attggcagtt      60
gttataggta ccccagtttt gttaagcgga gggactgcat tggccgctgc tgtaactgct     120
gaagagggca cgggctttgc tgcattgaag tttgcgcaag tgcctctaaa atatgctttt     180
aatgccttgg agcctaatat agatgcgctt actatggaca ttcattatac aaaacaccat     240
gcggcctatg ttaaaaatgt aaatgatgca attgcggccg aaaagattcc gtacaaaaca     300
gaggcggaat tttttaataa tgcttcgaag ctttcggcca agcacgtaa caatggtggt     360 ggggcatgga atcataattt ctttttttgag actttaaagc cagggggggc aactggacca     420
gaaggaaaat taaagatgc tattgtgaag tcatttgttt cggttgataa atttaaagaa     480 caatttctg ctgctgcggc atcacgtttt ggttcaggat gggcatggtt ggttaatgat     540
aagggaactt taaagatttg ttcgaccgct aatcaggata tcctttatt tgataatgcg     600 gaagtgaaag gcgtaccttt gttgggactt gatgtatggg agcacgctta ttatcttaag     660
tatcagaata aacgtgcaga ttatattgcc aactggtgga atgtcgtgga ttgggatgtg     720
gtgagtaaaa ggctgtag                                                   738

<210> SEQ ID NO 15
<211> LENGTH: 255
<212> TYPE: PRT
<213> ORGANISM: Mongoliicoccus sp-62519
<220> FEATURE:
<221> NAME/KEY: PEPTIDE
<222> LOCATION: (29)..(255)

<400> SEQUENCE: 15
```

Met Ser Asn Phe Ser Arg Arg Ser Phe Leu Thr Arg Thr Thr Lys Ala
1               5                   10                  15

Thr Leu Ala Val Gly Ile Gly Ser Ser Ala Leu Gly Ser Thr Leu Leu
            20                  25                  30

Ala Cys Asn Asn Ala Thr Thr Arg Gln Asp Glu Lys Ala Val Leu Asp
        35                  40                  45

Asn Leu Arg Thr Asp Phe Thr Gln Thr Asp Leu Pro Tyr Asp Tyr Ser
    50                  55                  60

Ala Leu Glu Pro His Ile Asp Ala Arg Thr Met Glu Ile His Tyr Ser
65                  70                  75                  80

Arg His Ala Lys Ser Tyr Ala Glu Asn Leu Arg Glu Ala Ala Glu Glu
                85                  90                  95

Glu Asp Val Asp Thr Ser Lys Pro Val Glu Glu Leu Met Met Asn Ile
            100                 105                 110

Ser His Tyr Ser Asp Lys Met Arg Asn Asn Gly Gly His Tyr Asn
        115                 120                 125

His Glu Leu Phe Trp Lys Ile Met Ser Pro Asp Gly Gly Gln Pro
    130                 135                 140

Gln Gly Glu Leu Ala Gln Ala Ile Asn Asn Ser Phe Gly Ser Tyr Asp
145                 150                 155                 160

Glu Phe Val Glu Lys Phe Glu Gln Glu Ala Lys Asp Arg Phe Gly Ser
                165                 170                 175

Gly Trp Ala Trp Leu Val Leu Asp Arg Asp Lys Asn Leu Ala Val Gly
            180                 185                 190

Ser Thr Pro Asn Gln Asp Asn Pro Leu Met Asn Asp Val Asp Phe Gln
            195                 200                 205

Gly Ile Pro Leu Met Gly Ile Asp Val Trp Glu His Ala Tyr Tyr Leu
    210                 215                 220

Lys Tyr Gln Asn Glu Arg Gly Glu Tyr Ile Ser Asn Trp Trp Asn Val
225                 230                 235                 240

Val Asp Trp Gln Thr Ile Ala Arg Arg Tyr Glu Lys Leu Arg Ala
            245                 250                 255

<210> SEQ ID NO 16
<211> LENGTH: 768
<212> TYPE: DNA
<213> ORGANISM: Mongoliicoccus sp-62519
<220> FEATURE:
<221> NAME/KEY: gene
<222> LOCATION: (1)..(768)

<400> SEQUENCE: 16

```
atgagcaatt tttcaagaag gagcttcctt acccgcacca ccaaagccac ccttgccgta      60
ggcataggct cctcagcact cggatccacc ctgctggcat gcaacaatgc caccacccgg     120
caggatgaaa aagcggtgct ggacaatctc aggacggact ttacccaaac tgatcttccc     180
tatgactaca gtgctttgga gccccatatc gacgcccgta caatggagat ccactactcc     240
agacatgcca aaagttatgc agagaaccta agggaagcag cggaggagga agacgtggac     300
acttctaagc cggtggaaga actgatgatg aacatcagcc attactcgga caagatgaga     360
aacaacgggg gaggccatta caaccatgag cttttctgga agatcatgtc tcccgacggc     420
ggtggccaac cgcaggggga gcttgcccag gccatcaaca attccttcgg cagctatgat     480
gaattcgtgg aaaaattcga acaggaagcc aaggaccgct tcggttcggg ctgggcttgg     540
ctcgtgctgg acagggacaa aaacctggcc gtgggctcca ccccaaacca ggacaatccg     600
```

```
ctgatgaatg acgtggattt ccagggcatt cccctgatgg gtatagatgt ttgggaacat    660
gcttattacc tcaaatatca gaacgaacgg ggggagtaca tttccaactg gtggaatgtc    720
gtcgactggc aaaccatagc ccggagatac gaaaaattaa gagcttaa                 768
```

```
<210> SEQ ID NO 17
<211> LENGTH: 249
<212> TYPE: PRT
<213> ORGANISM: Arcicella aquatica
<220> FEATURE:
<221> NAME/KEY: PEPTIDE
<222> LOCATION: (27)..(249)

<400> SEQUENCE: 17
```

```
Met Asn Arg Lys Ser Phe Leu Lys Thr Thr Leu Ala Ser Ala Phe Ala
1               5                   10                  15

Leu Ser Ser Leu Asn Ser Phe Ser Leu Arg Arg Ser Tyr Asn
            20                  25                  30

Asp Lys Leu Pro Lys Leu Thr Leu Glu Glu Val Met Leu Glu Ser Ala
        35                  40                  45

Pro Phe Ser Leu Ala Ala Leu Pro Tyr Ala Pro Asp Ser Leu Glu Pro
    50                  55                  60

Ser Ile Asp Lys Leu Thr Met Glu Ile His His Asp Arg His His Lys
65                  70                  75                  80

Ala Tyr Val Asp Asn Leu Asn Lys Ala Val Ala Gly Thr Pro Tyr Glu
                85                  90                  95

Lys Leu Ser Leu Trp Asp Leu Leu Lys Glu Ala Gly Lys Ala Pro Ala
            100                 105                 110

Ala Ile Arg Asn Asn Ala Gly Gly His Trp Asn His Thr Phe Phe Trp
        115                 120                 125

Asn Val Met Ser Pro Lys Ala Gly Gly Ser Pro Lys Gly Glu Leu Leu
    130                 135                 140

Asp Glu Ile Thr Lys Thr Phe Gly Ser Phe Asp Lys Phe Lys Glu Glu
145                 150                 155                 160

Phe Ala Lys Ala Gly Thr Thr Arg Phe Gly Ser Gly Trp Ala Trp Leu
                165                 170                 175

Ile Val Gln Asp Lys Lys Leu Val Ile Thr Ser Thr Pro Asn Gln Asp
            180                 185                 190

Asn Pro Leu Met Asp Val Ala Glu Lys Lys Gly Ser Pro Ile Leu Ala
        195                 200                 205

Leu Asp Val Trp Glu His Ala Tyr Tyr Leu Lys Tyr Gln Asn Lys Arg
    210                 215                 220

Ala Asp Tyr Ile Thr Ala Phe Trp Asn Val Val Asn Trp Asp Ala Val
225                 230                 235                 240

Ser Lys Asn Phe Glu Asn Leu Lys Lys
                245
```

```
<210> SEQ ID NO 18
<211> LENGTH: 750
<212> TYPE: DNA
<213> ORGANISM: Arcicella aquatica
<220> FEATURE:
<221> NAME/KEY: gene
<222> LOCATION: (1)..(750)

<400> SEQUENCE: 18
atgaaccgta aaagtttttt aaagacaaca ttagcatcgg cttttgcatt gtctagctta     60
aattcattca gttttncatt aagaagaagc tataatgaca aattacctaa attgacatta    120
```

```
gaagaagtaa tgcttgaatc agcgcctttc tctttagcag cgttgcctta tgcacctgat    180
agtttagagc cgagcattga taagttgacg atggagattc accatgatcg ccatcacaaa    240
gcatatgttg ataatttgaa taaagctgtg gctggtactc cttacgaaaa attatctttg    300
tgggatttat tgaaagaagc aggaaaagca ccagctgcta ttagaaataa tgcaggtgga    360
cattggaatc atacttttt ctggaatgta atgtcgccta aagctggagg ttctcccaaa     420
ggtgaattat tggatgaaat cactaaaacc tttggttcgt ttgataaatt caaagaagag    480
tttgctaaag ctggaactac tcgctttggt tcaggttggg cttggttaat tgttcaagat    540
aagaaattag tgattacttc aacgccaaat caagataacc ctttgatgga tgtggctgaa    600
aagaaaggtt cgccaatttt agccttagat gtttgggaac acgcttatta ccttaaatac    660
caaaacaaac gtgcggatta tcactgcg ttctggaatg tagtaaattg ggatgctgtt      720
tcaaagaatt ttgaaaactt gaagaaataa                                     750
```

```
<210> SEQ ID NO 19
<211> LENGTH: 251
<212> TYPE: PRT
<213> ORGANISM: Paraburkholderia sediminicola
<220> FEATURE:
<221> NAME/KEY: PEPTIDE
<222> LOCATION: (31)..(251)

<400> SEQUENCE: 19
```

Met Leu Asn Thr Leu Ile Ser Arg Arg His Leu Met Ala Ala Gly Ser
1               5                   10                  15

Met Ala Ser Phe Ser Val Leu Phe Ser Lys Leu Ala Tyr Gly Ala Ala
            20                  25                  30

Thr Gly Asp Ala Gly Pro Gly Ala Ser Thr Ala Thr Val Val Pro
        35                  40                  45

Ala Phe Leu Gly Ser Ser Pro Gln Thr Leu Pro Pro Leu Pro Trp Ala
    50                  55                  60

Asp Asn Ala Leu Glu Pro Thr Ile Ser Ala Arg Thr Ile Gly Ile His
65                  70                  75                  80

Tyr Gly Lys His His Arg Ala Tyr Phe Asp Asn Leu His Lys Leu Leu
                85                  90                  95

Ala Gly Thr Pro Leu Glu Gln Ala Ser Leu Glu Gln Ile Ile Met Gln
            100                 105                 110

Ser His Asp Gln Pro Ala Leu Ala Asp Val Phe Asn Asn Ala Ala Gln
        115                 120                 125

Ala Trp Asn His Asn Phe Tyr Trp Asn Ser Leu Ser Pro Ala Pro Ser
130                 135                 140

Ala Pro Ser Glu Lys Leu Gln Ala Ala Ile Thr Arg Lys Phe Gly Ser
145                 150                 155                 160

Val Asp Ala Leu Ala Lys Ala Leu Val Ala Thr Ser Ala Ser Gln Phe
                165                 170                 175

Gly Ser Gly Trp Gly Trp Leu Val Leu Asp Arg Gly Glu Leu Ala Val
            180                 185                 190

Val Lys Thr Ser Asn Ala Glu Thr Pro Phe Thr Arg Gly Leu Val Pro
        195                 200                 205

Leu Leu Thr Val Asp Val Trp Glu His Ala Tyr Tyr Leu Asp Tyr Gln
    210                 215                 220

Asn Arg Arg Pro Asp Tyr Leu Val Ala Thr Val Ser Arg His Leu Asn
225                 230                 235                 240

```
Trp Ala Phe Ala Ser Ala Asn Leu Asp Arg Gly
                245                 250
```

<210> SEQ ID NO 20
<211> LENGTH: 756
<212> TYPE: DNA
<213> ORGANISM: Paraburkholderia sediminicola
<220> FEATURE:
<221> NAME/KEY: gene
<222> LOCATION: (1)..(756)

<400> SEQUENCE: 20

```
atgctcaaca cccttatttc ccggcggcat ctgatggccg cgggatccat ggcctcattc      60
agcgtgctgt tttcgaagct tgcctacggc gcggccacag gcgacgccgg gcccggcgca     120
agcacggcga cgaccgtcgt cccggcattt ctcggctcgt cgccgcaaac actgccgccg     180
ctgccatggg ctgacaatgc gcttgagccg accatttcgg cgcgcaccat cggcattcat     240
tacggcaagc accaccgggc ctatttcgac aatctgcaca gcttcttgc cggcacgccg      300
ctcgaacagg catcgctcga acagatcatc atgcagtcgc atgaccagcc cgcgctcgca     360
gacgttttca caacgccgc gcaggcatgg aaccacaact tctactggaa ctcgctgagc      420
ccggcgccga gcgcgccgag cgagaaactt caggcggcga tcacccgcaa gttcggttcc     480
gtcgatgcac tcgcgaaggc gctcgtcgca acgtcggcat cgcagttcgg cagtggctgg     540
ggatggctcg tgctcgatcg cggagaactc gcggtcgtca agacgagcaa cgcggaaacg     600
ccgtttacgc gtggactcgt accgctgcta accgtggatg tatgggagca cgcgtactac     660
ctggactatc agaaccgtcg accggactat ctggtcgcga cggtctcgcg tcacctgaac     720
tgggcgttcg cctcagccaa tcttgaccgt ggctga                              756
```

<210> SEQ ID NO 21
<211> LENGTH: 202
<212> TYPE: PRT
<213> ORGANISM: Bacillus licheniformis
<220> FEATURE:
<221> NAME/KEY: PEPTIDE
<222> LOCATION: (1)..(202)

<400> SEQUENCE: 21

```
Met Ala Tyr Lys Leu Pro Glu Leu Pro Tyr Ala Tyr Asp Ala Leu Glu
1               5                  10                  15

Pro His Ile Asp Lys Glu Thr Met Asn Ile His His Thr Lys His His
            20                  25                  30

Asn Thr Tyr Val Thr Lys Leu Asn Glu Ala Val Ala Gly Lys Gln Asp
        35                  40                  45

Leu Glu Ser Lys Ser Val Glu Glu Leu Val Ala Asn Leu Asp Ala Val
    50                  55                  60

Pro Glu Asn Ile Arg Thr Ala Val Arg Asn Asn Gly Gly Gly His Ala
65                  70                  75                  80

Asn His Ser Leu Phe Trp Lys Leu Leu Ser Pro Asn Gly Gly Gly Ala
                85                  90                  95

Pro Thr Gly Glu Leu Ala Glu Ala Ile Asn Ser Lys Phe Gly Ser Phe
            100                 105                 110

Asp Gln Phe Lys Glu Asp Phe Ala Ala Ala Ala Gly Arg Phe Gly
        115                 120                 125

Ser Gly Trp Ala Trp Leu Val Val Asn Asn Gly Glu Leu Glu Ile Thr
    130                 135                 140

Ser Thr Pro Asn Gln Asp Ser Pro Leu Ser Glu Gly Lys Thr Pro Ile
```

-continued

```
            145                 150                 155                 160
Leu Gly Leu Asp Val Trp Glu His Ala Tyr Tyr Leu Asn Tyr Gln Asn
                    165                 170                 175

Arg Arg Pro Asp Tyr Ile Lys Ala Phe Trp Asn Val Val Asn Trp Asp
                180                 185                 190

Glu Val Ala Arg Leu Tyr Ser Glu Ala Lys
                195                 200
```